United States Patent
Wrobel et al.

(10) Patent No.: US 6,281,238 B1
(45) Date of Patent: Aug. 28, 2001

(54) 4-ARYL-1-OXA-9-THIA-CYLOPENTA[B] FLUORENES

(75) Inventors: Jay E. Wrobel, Lawrenceville; Zenan Li, Plainsboro, both of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/526,387

(22) Filed: Mar. 16, 2000

Related U.S. Application Data

(62) Division of application No. 09/307,820, filed on May 10, 1999, now Pat. No. 6,057,316.
(60) Provisional application No. 60/135,096, filed on May 12, 1998.

(51) Int. Cl.[7] .................. A61K 31/417; A61K 31/433; C07D 407/10; C07D 209/90
(52) U.S. Cl. .................. 514/396; 514/438; 514/468; 548/148; 548/250; 548/157; 548/127; 549/6
(58) Field of Search .................. 514/359, 360, 514/361, 396, 402, 430, 438, 443, 468; 548/250, 127, 148, 159; 549/6

(56) References Cited

PUBLICATIONS

Wrobel et al, Synthesis and PTP1B Inhibition, Bioorg. Med. Chem. Lett. (2000), vol. 10 issue 14, Oct. 2000.*
Ahmad, F. et al., Biochemica et Biophysica Acta, 1248, 1995, pp. 57–69.
Chang, A.Y. et al., Diabetes, 32, 1983, pp. 830–838.
Coleman, D.L., Diabetologia, 14, 1978, pp. 141–148.
DeFronzo, R. A. et al., Diabetes Care, 14:3, 1991, pp. 173–194.
Goldstein, B. J., Receptor, 3, 1993, pp. 1–15.
Goldstein, B.J. et al., Mol. and Cell. Biochem., 109, 1992, pp. 107–113.
Goldstein, B. J., J. Cell. Biochem., 48, 1992, pp. 33–42.
Haring, H. U., Diabetologia, 34, 1991, pp. 848–861.
Harris, M. I. et al., Diabetes in America, 1985, Chapter 29, pp. 1–48.
Jarrett, R. J., Diabetes/Metabolism Reviews, 5:7, 1989, pp. 547–558.
Kano, S. et al., Heterocycles, 19:6, 1982, pp. 1033–1037.
Lanzetta, P. A. et al., Analytical Biochem. 100, 1979, pp. 95–97.
Martin, S.F. et al., J. Org. Chem., 49, 1984, pp. 2512–2513.
McGuire, M. C. et al., Diabetes, 40, Jul. 1991, pp. 939–942.
Meyerovitch, J. et al., J. Clin. Invest., 87, Apr. 1991, pp. 1286–1294.
Meyerovitch, J. et al., J. Clin. Invest., 84, Sep. 1989, pp. 976–983.
Mitsunobu, O., Synthesis, Jan. 1981, pp. 1–28.
Nutaitis, C. F., Organic Preparations and Procedures Int., 23(4), 1991, pp. 403–411.
Perich, J. W. et al., Synthesis, Feb. 1988, pp. 142–144.
Phillion, D. P. et al., Tetrahedron, 27:13, 1986, pp. 1477–1480.
Pyorala, K. et al., Diabetes/Metabolism Reviews, 3:2, 1987, pp. 463–524.
Reaven, G. M. et al., Amer. J. Med., 60, 1976, pp. 80–88.
Sredy, J. et al., Metabolism, 44:8, 1995, pp. 1074–1081.
Stout, R. W., Metabolism, 34:12 (Suppl 1), Dec. 1985, pp. 7–12.
Zask, A. et al., J. Med. Chem., 33, 1990, pp. 1418–1423.

* cited by examiner

*Primary Examiner*—Alan L. Rotman
*Assistant Examiner*—Rita Desai
(74) *Attorney, Agent, or Firm*—Steven R. Eck

(57) ABSTRACT

This invention provides compounds of Formula I having the structure

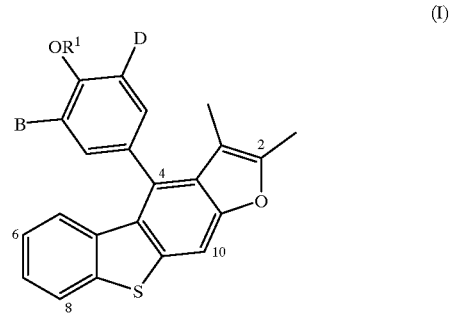

wherein
  B and D are each, independently, hydrogen, halogen, —CN, alkyl of 1–6 carbon atoms, aryl, or aralkyl of 6–12 carbon atoms;
  $R^1$ is hydrogen, alkyl of 1–6 carbon atoms, —CH($R^2$)W, —C($CH_3$)$_2$$CO_2$$R^3$, 5-thiazolidine-2,4-dione, —CH($R^4$)$CH_2$$CO_2$$R^3$, —COR$^3$, or —PO$_3$($R^3$)$_2$;
  $R^2$ is hydrogen, alkyl of 1–6 carbon atoms, aralkyl of 6–12 carbon atoms, aryl, —$CH_2$(1H-imidazol-4-yl), —$CH_2$(3-1H-indolyl), —$CH_2$$CH_2$(1,3-dioxo-1,3-dihydro-isoindol-2-yl), —$CH_2$$CH_2$(1-oxo-1,3-dihydro-isoindol-2-yl), or —$CH_2$(3-pyridyl);
  W is —$CO_2$$R^3$, —$CONH_2$, —CONHOH, —CN, CONH($CH_2$)$_2$CN, 5-tetrazole, or —PO$_3$($R^3$)$_2$;
  $R^3$ is hydrogen, alkyl of 1–6 carbon atoms, or aryl;
  $R^4$ is hydrogen or alkyl of 1–6 carbon atoms;
or a pharmaceutically acceptable salt thereof, which are useful in treating metabolic disorders related to insulin resistance or hyperglycemia.

7 Claims, No Drawings

4-ARYL-1-OXA-9-THIA-CYLOPENTA[B] FLUORENES

CROSS-REFERENCE

This application is a divisional of Ser. No. 09/307,820 filed May 10, 1999, U.S. Pat. No. 6,057,316, This application claims the benefit of Ser. No. 60/135,096 filed May 12, 1998 now abondoned.

This application claims the benefit of U.S. Provisional Application No. (not yet known), which was converted from U.S. patent application Ser. No. 09/076,623, filed May 12, 1998, pursuant to a petition filed under 37 C.F.R. 1.53(c)(2)(i) on Jul. 6, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989, 5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest*. 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

K. Shinzo, et al., *Heterocylces* 1982, 19, 1033–1037 disclosed a synthesis of benzo[b]naphtho[2,3-d]thiophenes of which two examples also had a 11-phenyl substituent as shown by structure A below. The compounds shown by structure A differ from that in the present invention in that the terminal furan ring of the compounds in the present invention is replaced by a benzene ring. None of these prior art compounds are for the indications of diabetes or PTPase inhibitors.

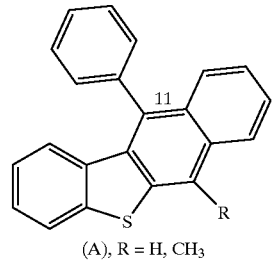

(A), R = H, CH$_3$

DESCRIPTION OF THE INVENTION

This invention provides compounds of Formula I having the structure

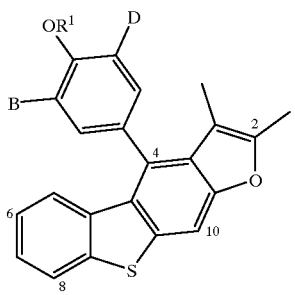

wherein
- B and D are each, independently, hydrogen, halogen, —CN, alkyl of 1–6 carbon atoms, aryl, or aralkyl of 6–12 carbon atoms;
- $R^1$ is hydrogen, alkyl of 1–6 carbon atoms, —CH($R^2$)W, —C(CH$_3$)$_2$CO$_2$R$^3$, 5-thiazolidine-2,4-dione, —CH(R$^4$)CH$_2$CO$_2$R$^3$, —COR$^3$, or —PO$_3$(R$^3$)$_2$;
- $R^2$ is hydrogen, alkyl of 1–6 carbon atoms, aralkyl of 6–12 carbon atoms, aryl, —CH$_2$(1H-imidazol-4-yl), —CH$_2$(3-1H-indolyl), —CH$_2$CH$_2$(1,3-dioxo-1,3-dihydro-isoindol-2-yl), —CH$_2$CH$_2$(1-oxo-1,3-dihydro-isoindol-2-yl), or —CH$_2$(3-pyridyl);
- W is —CO$_2$R$^3$, —CONH$_2$, —CONHOH, —CN, CONH(CH$_2$)$_2$CN, 5-tetrazole, or —PO$_3$(R$^3$)$_2$;
- $R^3$ is hydrogen, alkyl of 1–6 carbon atoms, or aryl;
- $R^4$ is hydrogen or alkyl of 1–6 carbon atoms;

or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety, such as when $R^2$ is CH$_2$(3-pyridyl) or contains similar basic moieties. Salts may also be formed from organic and inorganic bases, preferably alkali metal salts, for example, sodium, lithium, or potassium, when a compound of this invention contains a carboxylate or phenolic moiety.

Alkyl includes both straight chain as well as branched moieties. Halogen means bromine, chlorine, fluorine, and iodine. It is preferred that the aryl portion of the aryl or aralkyl substituent is a phenyl or naphthyl; with phenyl being most preferred. The aryl moiety may be optionally mono-, di-, or tri-substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The compounds of this invention may be atropisomers by virtue of possible restricted or slow rotation about the aryl-tetracyclic single bond. This restricted rotation creates additional chirality and leads to enantiomeric forms. If there is an additional chiral center in the molecule, diasteriomers exist and can be seen in the NMR and via other analytical techniques. While shown without respect to atropisomer stereochemistry in Formula I, the present invention includes such atoropisomers (enantiomers and diastereomers; as well as the racemic, resolved, pure diastereomers and mixtures of diasteomers) and pharmaceutically acceptable salts thereof.

Preferred compounds are those in which B and D are halogen; those in which $R^1$ is hydrogen or —CH(R$^2$)W; and those in which $R^1$ is hydrogen or —CH(R$^2$)W, wherein $R^2$ is hydrogen, alkyl of 1–6 carbon atoms, aralkyl of 6–12 carbon atoms, or aryl, W is —CO$_2$R$^3$, or CONH$_2$, and $R^3$ is hydrogen, or alkyl of 2–6 carbon atoms.

More preferred compounds of this invention are:

- ((R)-2-[4-(2,3-dimethyl-1-oxa-9-thia-cyclopenta[b]fluoren-4-yl)-2,6-diiodo-phenoxy]-3-phenyl-propionic acid; and
- (R)-2-[4-(2,3-dimethyl-1-oxa-9-thia-cyclopenta[b]fluoren-4-yl)-2,6-diiodo-phenoxy]-propionic acid.

The compounds of this invention can be prepared according to the following schemes from commercially available starting materials or starting materials which can be prepared using to literature procedures. These schemes show the preparation of representative compounds of this invention.

Scheme 1

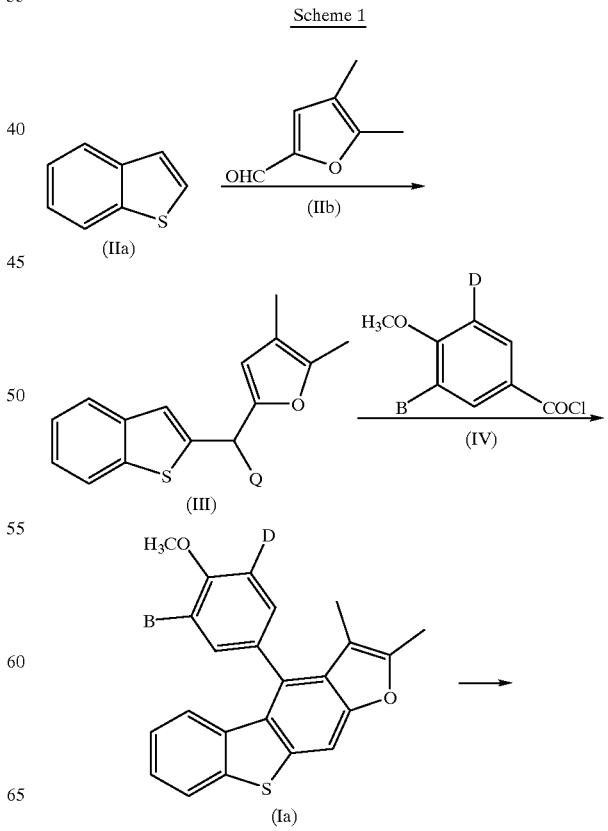

-continued

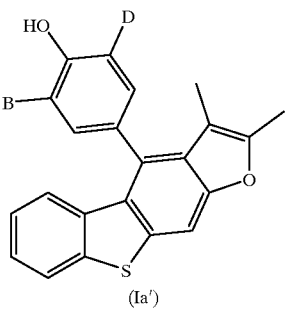
(Ia')

In Scheme 1, commercially available thianaphthene (IIa) is treated with one to 1.3 molar equivalents of an alkyl lithium reagent such as N-butyl lithium most preferably in a nonprotic solvent such as THF at temperatures ranging from −78° C. to room temperature under an inert atmosphere such as nitrogen or argon to provide the 2-lithiated-thianaphthene derivative. This lithiated analog is reacted in situ with one or more molar equivalents of 4,5-dimethyl-2-furanaldehyde (IIb) (prepared from Vilsmeir-Haack formylation of commercially available 4,5-dimethylfuraldehyde; S. F. Martin, et al. *J. Org. Chem.* 1984, 49, 2512–2516), generally at −78° C. to room temperature for 5 min to 3 h to provide the compound of formula (III: Q=OH). The hydroxy group (Q=OH) of (III) can be removed by a number of reduction procedures such as hydrogenation using palladium catalysts to produce the compound of formula (III: Q=H) but is most conveniently removed using a modification of the method of Nutaitis, et. al. (*Org. Prep. and Proceed. Int.* 1991, 23, 403–411) in which (III: Q=OH) is stirred with one to ten molar equivalents of sodium borohydride in a suitable solvent such as ether, THF, dichloromethane or carbon disulfide at 0° C. to room temperature and one to fifty molar equivalents of trifluoroacetic acid is slowly added over a 15 min to 3 h period to produce the compound of formula (III: Q=H).

The compounds of formula (III: Q=H) can be reacted with one or more molar equivalents of a commercially available benzoic acid chloride of formula (IV: B, D is H) to produce the cyclic derivative of formula (Ia: B, D is H). This reaction is accomplished most readily using a one to five molar equivalents of a Lewis acid catalyst such as tin tetrachloride or aluminum chloride in an inert solvent such as dichloromethane, 1,2-dichloroethane, ether or carbon disulfide, generally at temperatures ranging from −78° C. to room temperature.

In an analogous fashion to the reactions above in Scheme 1, the compounds of formula (Ia: B, D is lower alkyl) can be prepared starting from the compound of formula (III: Q is H) and the appropriate benzoic acid chloride (IV: B, D is lower alkyl). The benzoic acid chloride (IV: B, D is lower alkyl). is prepared from the corresponding benzoic acid by standard procedures using reagents such as oxalyl chloride and thionyl chloride. The starting benzoic acid of the benzoic acid chloride (IV: B, D is lower alkyl) is commercially available or can be easily prepared by known procedures. For example, the acid starting material for benzoic acid chloride (IV: B, D is isopropyl) can be prepared using a modification of the method of Schuster, et al., *J. Org. Chem* 1988, 53, 5819. Thus commercially available 2,6-diisopropyl phenol is brominated in the 4-position (bromine/acetic acid), methylated (iodomethane/potassium carbonate/DMF), reacted with n-butyl lithium to effect lithium halogen exchange and the resultant organolithium species is reacted with carbon dioxide to provide 3,5-diisopropyl, 4-methoxy benzoic acid.

The methyl ethers of formula (Ia: B, D is H, lower alkyl) can be demethylated to the phenols of formula (Ia': B, D is H, lower alkyl) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichoromethane at temperatures ranging from −78° C. to 50° C.

Scheme 2

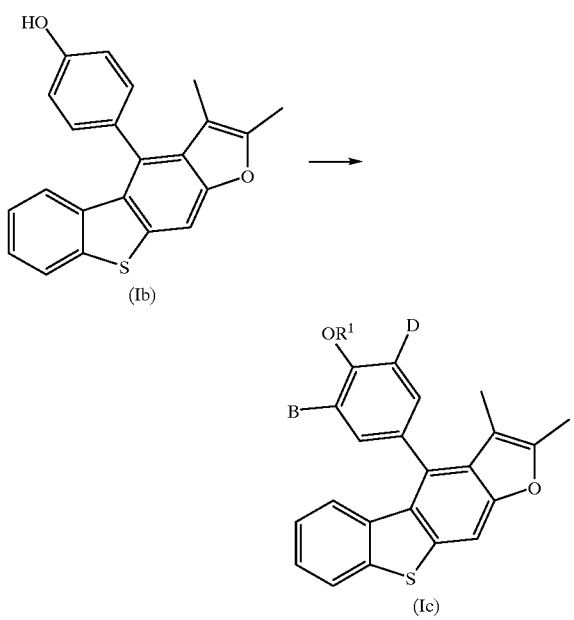

The phenol of formula (Ib) (Scheme 2) can be conveniently iodinated to the diiodophenol of formula (Ic: B, D is I; $R^1$ is H) using at least two molar equivalents of iodine in the presence of two or more molar equivalents of an alkali metal hydroxide such as NaOH in an alcohol solvent such as methanol at −20° C. to room temperature. Similarly the monoiodophenol (Ic: B is I; $R^1$, D is H) can be prepared from the phenol of formula (Ib) (Scheme 2) using one to 1.5 molar equivalents of iodine in the presence of at least one equivalent of an alkali metal hydroxide such as NaOH in an alcohol solvent such as methanol at −20° C. to room temperature. Either the monoiodophenol (Ic: B is I; $R^1$, D is H) or the diiodophenol (Ic: B, D is I; $R^1$ is H) can be converted to the respective methyl ether derivative of formula (Ic: B is I; D is H; $R^1$ is Me) or (Ic: B, D is I; $R^1$ is Me) by reacting the phenol moiety with a suitable methylating agent such as one or more molar equivalents of methyl iodide or dimethylsulfate employing a base such an alkali methyl carbonate or hydroxide such as potassium carbonate or sodium hydroxide in a suitable solvent such as THF, DMF or DMSO. The reaction is generally performed at temperatures ranging from 0° C. to 60° C.

The monoiodo methylether derivative of formula (Ic: B is I; D is H; $R^1$ is Me) or the diiodo methylether of formula (Ic:

B, D is I; $R^1$ is Me) can be reacted with one or more molar equivalents of copper (I) cyanide for the monoiodo analog or two or more molar equivalents of copper (I) cyanide for the diiodo derivative to produce the monocyanomethyl ether of formula (Ib: B is CN; D is H; $R^1$ is Me) or the dicyanomethyl ether of formula (Ib: B, D is CN; $R^1$ is Me). The cyanation reaction is generally performed at temperatures ranging from 100° C. to 250° C. employing polar aprotic solvents such as DMF, 1-methyl-2-pyrrolidinone or HMPA. Quinoline or pyridine can also be used.

The mono or dicyano methoxy analogs of formula (Ib: B is CN; D is H or CN; $R^1$ is Me) can be converted to the corresponding mono or dicyano phenol analogs of formula (Ic: B is CN; D is H or CN; $R^1$ is H) (Scheme 2) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

The monoiodo methylether derivative of formula (Ic: B is I; D is H; $R^1$ is Me) or the diiodo methylether of formula (Ic: B, D is I; $R^1$ is Me) (Scheme 2) can be reacted with one or more molar equivalents of copper (I) bromide for the monoiodo analog or two or more molar equivalents of copper (I) bromide for the diiodo derivative to produce the monobromo methyl ether of formula (Ic: B is Br; D is H; $R^1$ is Me) or the dibromo-methyl ether of formula (Ic: B, D is Br; $R^1$ is Me). The bromine/iodine exchange reaction is generally performed at temperatures ranging from 100° C. to 250° C. employing polar aprotic solvents such as DMF, 1-methyl-2-pyrrolidinone or HMPA. Quinoline or pyridine can also be used. The mono or dibromo methoxy analogs of formula (Ib: B is Br; D is H or Br; $R^1$ is Me) can be converted to the corresponding mono or dibromo phenol analogs of formula (Ib: B is Br; D is H or Br; $R^1$ is H) (Scheme 2) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

The phenols of formula (Ib: B, D is H, Br, I, CN, lower alkyl; $R^1$ is H) can be acylated on the phenolic oxygen using one or more molar equivalents of suitable acylating agent to provide the compounds of formula (Ib: B, D is H, Br, I, CN, lower alkyl; $R^1$ is OCOR; R is lower alkyl, aryl). The acylating agent is generally a lower alkyl or aryl carboxylic acid anhydride or a lower alkyl or aryl carboxylic acid chloride. The reaction is run under standard conditions such as using pyridine as solvent with or without a co-solvent such as dichloromethane at 0° C. to room temperature.

Scheme 3

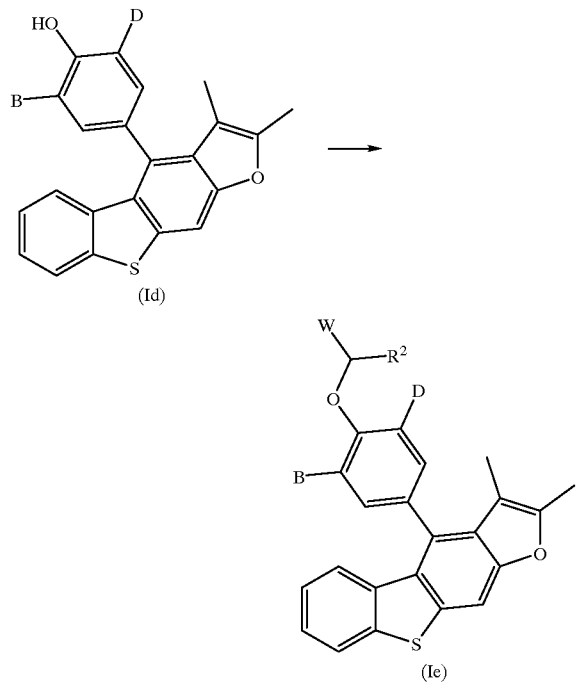

Further derivatives of the compounds of formula (I) in Scheme 3 can be prepared by the following methods. The phenols of formula (Id: B, D is H, Br, I, CN, lower alkyl) can be alkylated with one or more molar equivalents of an alkyl haloacetate of formula ($X^2CH_2CO_2R^3$ where $X^2$ is Cl, Br or I and $R^3$ is lower alkyl) and with one or more molar equivalents of an alkali metal carbonate such as potassium carbonate in a polar aprotic solvent such as DMF to afford the alkylated product of formula (Ie: B, D is H, Br, I, CN, lower alkyl; W is $CO_2R^3$; $R^3$ is H; $R^3$ is lower alkyl).

The phenols of formula (Id: B, D is H, Br, I, CN, lower alkyl) can be reacted with a 2-hydroxy carboxylic acid ester of formula CH(OH)($R^2$)$CO_2R^3$ ($R2$ is H, lower alkyl, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); $R^3$ is lower alkyl) to afford the esters of formula (Ie: B, D is H, Br, I, CN, lower alkyl; W is $CO_2R^3$; $R^2$ is H, lower alkyl, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); $R^3$ is lower alkyl) under the conditions of the Mitsunobu Reactions (for a review see Oyo Mitsunobu Synthesis. 1981, 1–27). The other co-reagents necessary to effect the Mitsunobu Reaction include one or more molar equivalents of a lower alkyl azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The 2-hydroxy carboxylic acid ester of formula CH(OH)($R^2$)$CO_2R^3$ ($R^2$ is H, lower alkyl, aralkyl, aryl, $CH_2$(1H-imidazol-4-yl), $CH_2$(3-1H-indolyl), $CH_2CH_2$(1,3-dioxo-1, 3-dihydro-isoindol-2-yl), $CH_2CH_2$(1-oxo-1,3-dihydro-isoindol-2-yl), $CH_2$(3-pyridyl); $R^3$ is lower alkyl) are commercially available or can be prepared from commercially available carboxylic acid precursors under standard esterification conditions. (S)-(+)-2-Hydroxy-1-oxo-3-dihydro-2-isoindolinebutyric acid, methyl ester can be prepared from (S)-(+)-2-hydroxy-1,3-dioxo-2-isoindolinebutyric acid, methyl ester via sequential treatment with 1) sodium borohydride in THF-water; 2) trifluoroacetic acid/chloroform; 3) triethylsilane/trifluoroacetic acid and 4) aqueous sodium bicarbonate. 3-(Pyridin-3-yl)-phenyllactic acid, ethyl ester can be prepared according to the two step procedure of B. A. Lefker, W. A. Hada, P. J. McGarry *Tetrahedron Lett.* 1994, 35, 5205–5208, from commercially available 3-pyridinecarboxaldehyde and ethyl chloroacetate.

The esters of formula (Ie: B, D is H, Br, I, CN, lower alkyl; W is $CO_2tBu$; $R^2$ is H) can be treated with one or more molar equivalents of a strong base such as lithium diisopropyl amide in a suitable solvent such as THF at temperatures ranging from −78° C. to room temperature. This procedure produces an anion alpha to the ester carbonyl. The resultant anion is treated with one or more molar equivalents of an alkyl halide of formula $X^2R^2$ (where $X^2$ is halogen; $R^2$ is alkyl and aralkyl) and warmed to room temperature to produce the alkylated ester of formula (Ie: B, D is H, Br, I, CN, lower alkyl; W is $CO_2tBu$; $R^2$ is alkyl and aralkyl).

The esters of formula (Ie: B, D is H, Br, I, CN, lower alkyl; W is $CO_2R^3$; $R^2$ is H, lower alkyl, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); $R^3$ is lower alkyl) can be transformed into their carboxylic acid analogs using standard conditions to afford the carboxylic acids of formula (Ie: B, D is H, Br, I, CN, lower alkyl; W is $CO_2H$; $R^2$ is H, lower alkyl, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl)). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Alternatively, acid conditions may also be employed in which the above mentioned carboxylic acid ester of formula (Ie) is reacted with one or more molar equivalents of a mineral acid such as HCl or sulfuric acid in water with or without a co-solvent such as THF at temperatures ranging from room temperature to 80° C. Still alternatively, many other conditions may be employed to effect the above mentioned ester to acid transformation leading to (Ie). These include reacting the carboxylic acid ester of formula (Ie) with one or more molar equivalents of boron tribromide or boron trichloride in dichloromethane at −78° C. to room temperature; one or more molar equivalents hydrobromic acid in acetic acid at 0° C. to 50° C.; one or more molar equivalents trimethylsilylbromide or trimethylsilyliodide in dichloromethane, carbon tetrachloride or acetonitrile at −78° C. to 50° C.; one or more molar equivalents lithium iodide in pyridine or quinoline at temperatures from 1000° to 250° C.

The phenols of formula (Id: B, D is H, Br, I, CN, lower alkyl) can be alkylated with one or more molar equivalents of diethyl trifluoromethyl sulfonyloxy methylphosphanate (D. P. Phillion and S. S. Andrew *Tet. Lett.* 1986, 1477–1480) and with one or more molar equivalents of an alkali metal hydride such as sodium hydride in a suitable solvent such as THF or DMF to afford the diethylphosphonate product of formula (Ie: B, D is H, Br, I, CN, lower alkyl; W is $PO_3Et_2$; $R^2$ is H).

The phenols of formula (Id: B, D is H, Br, I, CN, lower alkyl) can be reacted with a 2-hydroxy phosphonic acid diester of formula $CH(OH)(R^2)PO_3(R^3)_2$, ($R^2$ is H, lower alkyl, aralkyl, aryl, $R^3$ is lower alkyl)) to afford the phosphonic acid diesters of formula (Ie: B, D is H, Br, I, CN, lower alkyl; W is $PO_3(R^3)_2$; $R^2$ is H, lower alkyl, aralkyl, aryl, $R^3$ is lower alkyl) under the conditions of the Mitsunobu Reactions (for a review see Oyo Mitsunobu *Synthesis* 1981, 1–27). The other co-reagents necessary to effect the Mitsunobu Reaction include one or more molar equivalents of a lower alkyl azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The 2-hydroxy phosphonic acid diester of formula $CH(OH)(R^2)PO_3R^3$($R^2$ is H, lower alkyl, aralkyl, aryl; $R^3$ is lower alkyl) can be prepared by reacting a dialklylphosphonate of formula $HP(O)(OR^3)_2$($R^3$ is lower alkyl) with an aldehyde of formula $R^2CHO$ ($R^2$ is lower alkyl, aryl, aralkyl) under standard conditions.

The phosphonic acid diesters of formula (Ie: B, D is H, Br, I, CN, lower alkyl; W is $PO_3(R^3)_2$; $R^2$ is H, lower alkyl, aralkyl, aryl, $R^3$ is lower alkyl) can be transformed into their phosphonic acid analogs using standard conditions to afford the phosphonic acids of formula (Ie: B, D is H, Br, I, CN, lower alkyl; W is $PO_3H_2$; $R^2$ is H, lower alkyl, aralkyl, aryl). The conditions that may also be employed in which the above mentioned phosphonic acid diester of formula (Ie) is reacted with two or more molar equivalents of a mineral acid such as HCl or sulfuric acid in water with or without a co-solvent such as THF at temperatures ranging from 40 to 100° C. Still alternatively, many other conditions may be employed to effect the above mentioned diester to acid transformation leading to (Ie). These include reacting the phosphonic acid diester of formula (Ie) with two or more molar equivalents of boron tribromide or boron trichloride in dichloromethane at −78° C. to room temperature; two or more molar equivalents hydrobromic acid in acetic acid at 0° C. to 50° C.; two or more molar equivalents trimethylsilylbromide or trimethylsilyliodide in dichloromethane, carbon tetrachloride or acetonitrile at −78° C. to 50° C.; two or more molar equivalents lithium iodide in pyridine or quinoline at temperatures from 60° to 250° C.

The esters of formula (Ie: B, D is H, Br, I, CN, lower alkyl; W is $CO_2R^3$; $R^2$ is H, lower alkyl, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); $R^4$ is lower alkyl) can be transformed into their primary carboxylic acid amide analogs of formula (Ie: B, D is H, Br, I, CN, lower alkyl; W is $CONH_2$; $R_2$ is H, lower alkyl, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl)) by reacting the ester starting material with ammonia gas dissolved in a lower alcohol solvent such as methanol or ethanol at temperatures ranging from 0° C. to 100° C.

Alternatively, the carboxylic acids of formula (Ie: B, D is H, Br, I, CN, lower alkyl; W is $CO_2H$; $R^2$ is H, lower alkyl, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl)) can be transformed into their carboxylic acid amide analogs of formula (Ie: B, D is H, Br, I, CN, lower alkyl; W is $CONH_2$; $R^2$ is H, lower alkyl, aralkyl, aryl, $CH_2$(1H-imidazol-4-yl), CH₂(3-1H-indolyl), CH₂CH₂(1,3-dioxo-1,3-dihydro-isoindol-2-yl), CH₂CH₂(1-oxo-1,3-dihydro-isoindol-2-yl), CH₂(3-pyridyl)). This transformation can be accomplished using standard methods to effect carboxylic acid to carboxylic acid amide transformations. These methods include converting the acid to an activated acid and reacting with one or more molar equivalents of the desired amine. Amines in this category include ammonia in the form of ammonium hydroxide, hydroxyl amine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C.

The phenols of formula (Id: B, D is H, Br, I, CN, lower alkyl) can be alkylated with one or more molar equivalents of a haloacetonitrile of formula (X²CH₂CN where X² is Cl, Br or I) and with one or more molar equivalents of an alkali metal carbonate such as potassium carbonate in a polar aprotic solvent such as DMF to afford the nitrites of formula (Ie: B, D is H, Br, I, CN, lower alkyl W is CN; R²is H).

Alternatively, the carboxylic acid amide analogs of formula (Ie: B, D is H, Br, I, CN, lower alkyl; W is CONH₂; R² is H, lower alkyl, aralkyl, aryl, CH₂(1H-imidazol-4-yl), CH₂(3-1H-indolyl), CH₂CH₂(1,3-dioxo-1,3-dihydro-isoindol-2-yl), CH₂CH₂(1-oxo-1,3-dihydro-isoindol-2-yl), CH₂(3-pyridyl)) can be converted to their nitrile analogs of formula (Ie: B, D is H, Br, I, CN, lower alkyl; W is CN; R² is H, lower alkyl, aralkyl, aryl, CH₂(1H-imidazol-4-yl), CH₂(3-1H-indolyl), CH₂CH₂(1,3-dioxo-1,3-dihydro-isoindol-2-yl), CH₂CH₂(1-oxo-1,3-dihydro-isoindol-2-yl), CH₂(3-pyridyl)) by using reagents that dehydrate the primary carboxamide function to the nitrile function. One set of conditions to effect this transformation include reacting the said primary carboxylic acid amide with one or more molar equivalents of trifluoroacetic anhydride and two or more molar equivalents of pyridine in a suitable solvent such as dioxane at temperatures ranging from 60° C. to 120° C.

The nitrites analogs of formula (Ie: B, D is H, Br, I, CN, lower alkyl; W is CN; R² is H, lower alkyl, aralkyl, aryl, CH₂(1H-imidazol-4-yl), CH₂(3-1H-indolyl), CH₂CH₂(1,3-dioxo-1,3-dihydro-isoindol-2-yl), CH₂CH₂(1-oxo-1,3-dihydro-isoindo-2-yl), CH₂(3-pyridyl)) can be converted to the tetrazoles of formula (Ie: B, D is H, Br, I, CN, lower alkyl; W is 5-tetrazole; R² is H, lower alkyl, aralkyl, aryl, CH₂(1H-imidazol-4-yl), CH₂(3-1H-indolyl), CH₂CH₂(1,3-dioxo-1,3-dihydro-isoindol-2-yl), CH₂CH₂(1-oxo-1,3-dihydro-isoindol-2-yl), CH₂(3-pyridyl)) by reacting the nitrile function with one or more molar equivalents of trimethylaluminum and one or more molar equivalents of trimethylsilyl azide in a suitable solvent such as benzene or toluene at temperatures ranging from 60° C. to 120° C. Alternatively, the nitrile function can be reacted with one or more molar equivalents of ammonium azide in a suitable solvent such as dimethylformamide at temperatures ranging from 60° C. to 160° C.

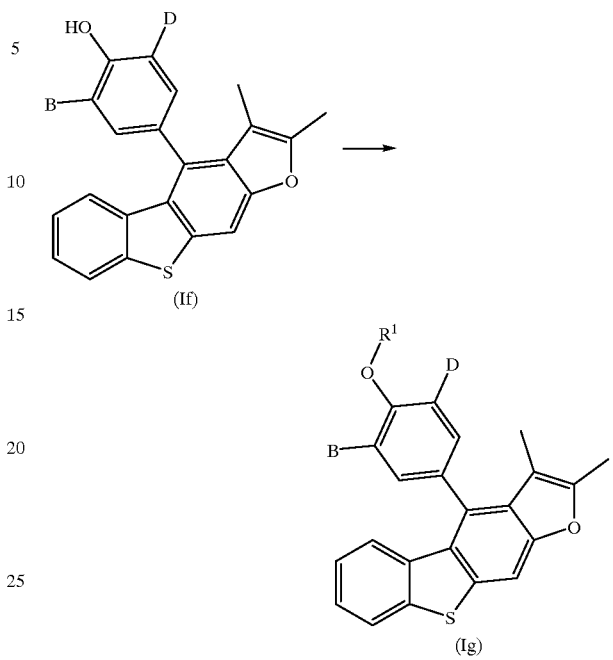

Scheme 4

Further derivatives of the compounds of formula (I) in Scheme 4 can be prepared by the following methods. The phenols of formula (If: B, D is H, Br, I, CN, lower alkyl) can be reacted with one or more molar equivalents of lithium (bis)trimethylsilylamide at temperatures ranging from –78° C. to room temperature and the lithium salt can be further reacted with one or more molar equivalents of 5-bromothiazolidine-2,4-dione (prepared according to the method of Zask, et al., J. Med Chem, 1990, 33, 1418–1423) using a suitable solvent such as THF under an inert atmosphere at temperatures ranging from –78° C. to room temperature to provide the compounds of formula (Ig: R¹ is (R, S)-5-thiazolidine-2,4-dione; B, D is H, Br, I, CN, lower alkyl).

Alternatively, the phenols of formula (If: B, D is H, Br, I, CN, lower alkyl) can be reacted with one or more molar equivalents of tetrazole and di-tert-butyl N,N-diethylphosporamidate in THF at room temperature followed by addition of one or more molar equivalents of meta-chlorobenzoic acid at –40° C. according to the procedure of J. W. Perich and R. B. Johns, Synthesis, 1988, 142–144) to afford the phosphate diesters of formula (Ig: R¹ is P(O)(OtBu)₂; B, D is H, Br, I, CN, lower alkyl). These phosphate diesters are then treated with one or more molar equivalents hydrochloric acid in a suitable solvent such as dioxane to provide the phosphonic acids of formula (Ig: R¹ is P(O)(OH)₂; B, D is H, Br, I, CN, lower alkyl).

The phenols of formula (If: B, D is H, Br, I, CN, lower alkyl) can be transformed to the carboxylic acids of formula (Ig: R¹ is C(CH₃)₂CO₂H; B, D is H, Br, I, CN, lower alkyl) by treatment of the phenols with two or more molar equivalents of solid sodium hydroxide followed by one or more molar equivalents of 1,1,1-trichloro-2-methyl-2-propanol tetrahydrate in the presence of a large excess of acetone which also serves as solvent.

The phenols of formula (If: B, D is H, Br, I, CN, lower alkyl) can be transformed to the carboxylic acids of formula (Ig: R¹ is CH₂CH₂CO₂H; B, D is H, Br, I, CN, lower alkyl)

by treatment with one or more molar equivalents of β-propiolactone and treatment with one or more molar equivalents of potassium tert-butoxide in a suitable solvent such as THF.

The phenols of formula (If: B, D is H, Br, I, CN, lower alkyl) can be reacted with a 3-hydroxy carboxylic acid ester of formula $CH(OH)(R^4)H_2CO_2R^3$ ($R^4$ is H or lower alkyl; $R^3$ is lower alkyl) to afford the esters of formula (Ig: $R^1$ is (R)-$CH(R^4)CH_2CO_2R^3$; B, D is H, Br, I, CN, lower alkyl; $R^4$ is H or lower alkyl; $R^3$ is lower alkyl) under the conditions of the Mitsunobu Reactions (for a review see Oyo Mitsunobu *Synthesis* 1981, 1–27). The other co-reagents necessary to effect the Mitsunobu Reaction include one or more molar equivalents of a lower alkyl azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C. at temperatures ranging from −20° C, to 120° C.

The 3-hydroxy carboxylic acid ester of formula CH(OH) $(R^4)CH_2CO_2R^3$ ($R^4$ is H or lower alkyl; $R^3$ is lower alkyl) are commercially available or can be prepared from commercially available carboxylic acid precursors under standard esterification conditions.

The esters of formula (Ig: $R^1$ is (R)—$CH(R^4)CH_2CO_2R^3$; B, D is H, Br, I, CN, lower alkyl; $R^4$ is H or lower alkyl; $R^4$ is lower alkyl) can be transformed to the acids of formula (Ig: $R^1$ is (R)—$CH(R^{44})CH_2CO_2H$; B, D is H, Br, I, CN, lower alkyl; $R^4$ is H or lower alkyl) by several standard conditions which include reacting the ester of formula (Ig) with two or more molar equivalents of a mineral acid such as HCl or sulfuric acid in one or more solvents or a combination of two or more solvents such as water, THF or dioxane at temperatures ranging from 40 to 120° C. Still alternatively, many other conditions may be employed to effect the above mentioned ester to acid transformation leading to (Ig). These include reacting the esters of formula (Ig) with two or more molar equivalents of boron tribromide or boron trichloride in dichloromethane at −78° C. to room temperature; two or more molar equivalents hydrobromic acid in acetic acid at 0° C. to 50° C.; two or more molar equivalents trimethylsilylbromide or trimethylsilyliodide in dichloromethane, carbon tetrachloride or acetonitrile at −78° C. to 50° C.; two or more molar equivalents lithium iodide in pyridine or quinoline at temperatures from 60° to 250° C.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following two standard pharmacological test procedures which measure the inhibition of PTPase.

Inhibition of Tri-phosphorvlated Insulin Receptor Dodecaphosphopeptide Dephosphorylation by Rat Hepatic Protein-tyrosine Phosphatases (PTPases)

This standard pharmacological test procedure assess the inhibition of rat hepatic microsomal PTPase activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly outlined below.

Preparation of Microsomal Fraction:

Rats (Male Sprague-Dawley rats (Charles River, Kingston, N.Y.) weighing 100–150 g, maintained on standard rodent chow (Purina)) are sacrificed by asphyxiation with CO2 and bilateral thoracotomy. The liver is removed and washed in cold 0.85% (w/v) saline and weighed. The tissue is homogenized on ice in 10 volumes of Buffer A and the microsomes are isolated essentially as described by Meyerovitch J, Rothenberg P, Shechter Y, Bonner-Weir S, Kahn C R. Vanadate normalizes hyperglycemia in two mouse models of non-insulin-dependent diabetes mellitus. *J Clin Invest* 1991; 87:1286–1294 and Alberts B, Bray D, Lewis J, Raff M, Roberts K, Watson J D, editors. Molecular biology of the cell. New York: Garland Publishing, Inc., 1989 with minor modifications. The liver homogenate is filtered through silk to remove any remaining tissue debris and then is centrifuged at 10,000×g for 20 minutes at 40° C. The supernatant is decanted and centrifuged at 100,000×g for 60 minutes at 40° C. The pellet, microsomes and small vesicles, is resuspended and lightly homogenized in: 20 mM TRIS-HCl (pH 7.4), 50 mM 2-mercaptoethanol, 250 mM sucrose, 2 mM EDTA, 10 mM EGTA, 2 mM AEBSF, 0.1 mM TLCK, 0.1 mM TPCK, 0.5 mM benzamidine, 25 ug/ml leupeptin, 5 ug/ml pepstatin A, 5 ug/ml; H5B antipain, 5 ug/ml chymostatin, 10 ug/ml aprotinin (Buffer A), to a final concentration of approximately 850 ug protein/ml. Protein concentration is determined by the Pierce Coomassie Plus Protein Assay using crystalline bovine serum aIbumin as a standard (Pierce Chemical Co., Rockford, Ill.).

Measurement of PTPase activity:

The malachite green-ammonium molybdate method, as described by Lanzetta P A, Alvarez L J, Reinach P S, Candia O A was used. An improved assay for nanomolar amounts of inorganic phosphate. *Anal. Biochem.* 1979;100:95–97, and adapted for the platereader, is used for the nanomolar detection of liberated phosphate by rat hepatic microsomal PTPases. The test procedure uses, as substrate, a dodeca-phosphopeptide custom synthesized by AnaSpec, Inc. (San Jose, Calif.). The peptide, TRDIYETDYYRK, corresponding to the 1142–1153 catalytic domain of the insulin receptor, is tyrosine phosphorylated on the 1146, 1150 and 1151 tyrosine residues. The microsomal fraction (83.25 ul) is preincubated for 10 min at 37 deg.C with or without test compound (6.25 ul) and 305.5 ul of the 81.83 mM HEPES reaction buffer, pH 7.4. Peptide substrate, 10.5 ul at a final concentration of 50 uM, is equilibrated to 37 deg.C in a LABLINE Multi-Blok heater equipped with a titerplate adapter. The preincubated microsomal preparation (39.5 ul) with or without drug is added to initiate the dephosphorylation reaction, which proceeds at 37 deg.C for 30 min. The reaction is terminated by the addition of 200 ul of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 ul MG/AM/Tw to substrate and followed by 39.5 ul of the preincubated membrane with or without drug. The color is allowed to develop at room temperature for 30 min and the sample absorbances are determined at 650 nm using a platereader (Molecular Devices). Samples and blanks are prepared in quadruplicates. Screening activity of 50 uM (final) drug is accessed for inhibition of microsomal PTPases.

Calculations:

PTPase activities, based on a potassium phosphate standard curve, are expressed as nmoles of phosphate released/ min/mg protein. Test compound PTPase inhibition is calculated as percent of control. A four parameter non-linear logistic regression of PTPase activities using SAS release 6.08, PROC NLIN, is used for determining IC50 values of test compounds. All compounds were administered at a concentration of 50 µM. The following results were obtained using representative compounds of this invention.

| Example | % Change from Control |
|---|---|
| 8 | −58.84 |
| 9 | −72.70 |
| Phenylarsine oxide (reference standard) | −57.06 |

Inhibition of Tri-Phosphorvlated Insulin Receptor Dodecaphosphopeptide Dephosphorylation by hPTP1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell. Biochem.* 109, 107, 1992). The enzyme preparation used was in microtubes containing 500–700 µg/ml protein in 33 mM Tris-HCl, 2 mM EDTA, 10% glycerol and 10 mM 2-mercaptoethanol.

Measurement of PTPase activity.

The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.). the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.

Calculations:

PTPase activities, based on a potassium phosphate standard curve, are expressed as nmoles of phosphate released/min/mg protein. Inhibition of recombinant PTP1B by test compounds is calculated as percent of phosphatase control. A four parameter non-linear logistic regression of PTPase activities using SAS release 6.08, PROC NLIN, is used for determining $IC_{50}$ values of test compounds. The following results were obtained.

| Example | IC50 (µM) |
|---|---|
| 8 | 0.284 |
| 9 | 0.074 |
| Phenylarsine oxide (reference standard) | 39.7 |
| Sodium orthovanadate (reference standard) | 244.8 |
| Ammonium molybdate tetrahydrate (reference standard) | 8.7 |

The blood glucose lowering activity of a representative compound of this invention was demonstrated in an in vivo standard procedure using diabetic (ob/ob) mice. The procedures used and results obtained are briefly described below.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978].

In each test procedure, mice [Male or female ob/ob (C57 Bl/6J) and their lean litermates (ob/+ or +/+, Jackson Laboratories) ages 2 to 5 months (10 to 65 g)] of a similar age were randomized according to body weight into 4 groups of 10 mice. The mice were housed 5 per cage and are maintained on normal rodent chow with water ad libitum. Mice received test compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety. The positive control, ciglitazone (5-(4-(1-methylcyclohexylmethoxy)benzyl)-2,4-dione, see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice received vehicle only.

On the morning of Day 4, 7 or 14 two drops of blood (approximately 50 ul) were collected into sodium fluoride containing tubes either from the tail vein or after decapitation. For those studies in which the compound was administered daily by gavage the blood samples were collected two hours after compound administration. The plasma was isolated by centrifugation and the concentration of glucose is measured enzymatically on an Abbott V.P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups (CMS SAS Release 5.18).

The results shown in the table below shows that the compounds of this invention are antihyperglycemia agents as they lower blood glucose levels in diabetic mice.

| Example | Dose (mg/Kg) | % Change Glucose from Vehicle | % Change Insulin from Vehicle |
| --- | --- | --- | --- |
| 9 | 10 | 8.13(a) | −43.43 |
| Ciglitazone (reference standard) | 100 | −43 | −39 | a - no significant activity (p < 0.05) at this dose.
b - not measured

Based on the results obtained in the standard pharmacological test procedures, representative compounds of this invention have been shown to inhibit PTPase activity and lower blood glucose levels in diabetic mice, and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, , xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1
4,5-Dimethyl-2-furaldehyde

According to the procedure of S. F. Martin, et al. *J. Org. Chem*. 1984, 49, 2512–2516, phosphorus oxychloride (10.7 mL, 114.4 mmol) was added dropwise to a stirred, ambient temperature solution of 2,3-dimethylfuran (10 g, 104 mmol) in DMF (150 mL) under a dry nitrogen atmosphere over a period of 30 min. After 3 h., the reaction mixture was hydrolized with 2.5 N aq. sodium hydroxide and further diluted with water (50 mL). Aqueous mixture was extracted with dichloromethane (2×300 mL). The combined dichloromethane extracts were washed with water, dried with brine and purified by silica gel flash chromatography (eluent: ethyl acetate) to provide a yellow oil (9.8 g, 76%); MS (ESI): [M+H]+, 125.1.

EXAMPLE 2
Benzo[b]thiophen-2-yl-(2,3-dimethyl-furan-5-yl)-methanol n-Butyl lithium (2.5 N in hexanes, 32.2 mL, 80.5 mmol) was added to a stirred solution of thianaphthene (10.6 g, 78.9 mmol) in THF (290 mL) at −78° C. After 15 min., a solution of 4,5-dimethyl-2-furaldehyde (9.79 g, 78.9 mmol) in THF (10 mL) was added. After additional 1 hour, the reaction mixture was quenched with 10% aqueous ammonium chloride (150 mL) and further diluted with water (150 mL). Aqueous mixture was extracted with dichloromethane. The combined dichloromethane extracts were washed with water, dried with brine and anhydrous Na2SO4, and concentrated to provide the title compound as an yellow oil (20.84 g, 100%): NMR (DMSO-d6); δ 7.89 (d, J=8 Hz, 1H), 7.76 (d, J=8, Hz, 1H), 7.35–7.26 (m, 2H), 7.25 (s, 1H), 6.36 (s, 1H), 6.08 (s, 1H), 5.92 (s, 1H), 2.13 (s, 3H), 1.86 (s, 3H); MS (EI): [M+], 258.

EXAMPLE 3
Benzo[b]thiophen-2-yl-(2,3-dimethyl-furan-5-yl)-methane

Trifluoroacetic acid (30 mL) was added dropwise to a rt, stirred suspension of benzo [b]thiophen-2-yl-(2,3-dimethyl-furan-5-yl)-methanol (9.56 g, 40.0 mmol) and sodium borohydride (7.0 g, 200 mL) in carbon disulfide (100 mL) under a try N2 atmosphere over a period of 30 min. After an additional 3 hours , the reaction mixture was carefully quenched and further diluted with aqueous ammonium chloride (250 mL). Aqueous mixture was extracted with ethyl ether (500 mL). The ethyl ether extract was washed with water and brine. Silica gel (100 mL) was added. Solvents were removed and the silica adsorbate was flash chromatographed (eluent 99:1 petroleum ether:ethyl acetate) to provide the title compound as an oil (3.75 g, 42%): NMR (CDCl3); δ 7.74 (d, J=8 Hz, 1H), 7.67 (d, J=8, Hz, 1H), 7.35–7.22 (m, 2H), 7.08 (d, J=1 Hz, 1H), 5.93 (s, 1H), 4.15 (s, 2H), 2.17 (s, 3H), 1.90 (s, 3H); MS (EI): [M+], 242.

EXAMPLE 4
4-(2,3-dimethyl-1-oxa-9-thia-cyclopenta[b]fluoren-4-yl)-phenyl methyl ether Tin tetrachloride (7.6 mL, 65.2 mmnol) was added dropwise to a −78° C., stirred solution of benzo[b]thiophen-2- yl-(2,3-dimethyl-furan-5-yl)-methane (3.96 g, 16.3 mmol) and anisoyl chloride (3.07 g, 17.93 mL) in carbon disulfide (100 mL) under a try N2 atmosphere over a period of 30 min. After the addition completed, the solution was allowed to warm to 0° C. After 9 h. the reaction mixture was carefully quenched with and further diluted with water (350 mL). Aqueous mixture was extracted with ethyl ether. The ethyl ether extracts were washed with water, 10% aqueous sodium bicarbonate and water and dried with brine. Silica gel (90 mL) was added. Solvents were removed and the silica adsorbate was flash chromatographed (eluent 99:1 petroleum ether:ethyl acetate) to provide the title compound as a light yellow solid (1.1 g, 25%): NMR (CDC13); δ 7.81 (s, 1H), 7.76 (d, J=8, Hz, 1H), 7.36–7.24 (m, 3H), 7.11–7.00 (m, 3H), 6.85 (d, J=8 Hz, 1H), 3.96 (s, 3H), 2.37 (s, 3H), 1.55 (s, 3H); MS (EI): [M+], 358.

EXAMPLE 5

4-(2.3-Dimethyl-1-oxa-9-thia-cyclopenta[b]fluoren-4-yl)-phenol

Boron tribromide (1.0 M solution in methylene chloride, 14.7 mL, 14.7 mmol) was added dropwise to a −78° C., stirred solution of 4-(2,3-dimethyl-1-oxa-9-thia-cyclopenta [b]fluoren-4-yl)-phenyl methyl ether (1.05 g, 2.9 mmol) in methylene chloride (42 mL) under a try N2 atmosphere. After 40 min., the solution was allowed to warm to ambient temperature. After 2.5 h. the reaction mixture was carefully quenched with 10% aqueous sodium bisulfide and further diluted with water (150 mL). Aqueous mixture was extracted with methylene chloride (300 mL). The methylene chloride extract was washed with water and dried with brine. Silica gel (25 mL) was added. Solvents were removed and the silica adsorbate was flash chromatographed (eluent 85:15 petroleum ether:ethyl acetate) to provide the methyl ester as a brown solid (0.951 g, 94%).: mp 174–175° C.: NMR (CDC13): δ 7.81 (s, 1H), 7.76 (d, J=8, Hz, 1H), 7.31–7.27 (m, 3H), 7.08–7.00 (m, 3H), 6.87 (d, J=8 Hz, 1H), 5.00 (s, 1H), 2.37 (s, 3H), 1.58 (s, 3H); MS (EI): [M+], 344.

EXAMPLE 6

4-(2,3-Dimethyl-1-oxa-9-thia-cyclopenta[b]fluoren-4-yl)-2,6-diiodo-phenol

Iodine (0.701 g, 2.76 mmol) was added portionwise to a stirred, 0° C. solution of 4-(2,3-dimethyl-1-oxa-9-thia-cyclopenta[b]fluoren-4-yl)-phenol (0.336 g, 1.06 mmol), sodium hydroxide (97%, 0.087 g, 2.12 mmol) in methanol (17 mL) over a period of 30 min. and the mixture was stirred at 0° C. for 2.5 h. and at ambient temperature for 15 h. The reaction mixture was quenched with 10% aqueous hydrochloride to pH 1 and diluted with water. Aqueous mixture was extracted with ethyl acetate (100 mL). The ethyl acetate was washed with 5% sodium bisulfite (50 mL) and water and dried with brine. Silica gel (8 mL) was added. Solvent was removed and the adsorbate was flash chromatographed (eluent 75:25 petroleum ether: methylene chloride) to provide the title compound as a white solid (0.34 g, 54%): NMR (CDC13); δ 7.83 (s, 1H), 7.81 (s, 2H), 7.80 (d, J=8, Hz, 1H), 7.33 (dd, J=8, 7, Hz, 1H), 7.15 (dd, J=8, 7, Hz, 1H), 6.98 (d, J=8 Hz, 1H), 5.99 (s, 1H), 2.37 (s, 3H), 1.61 (s, 3H); MS (EI): [M+], 596.

EXAMPLE 7

(S)-2-Hydroxy-3-phenylpropionic acid, methyl ester

A solution of commercially available (S)-2-hydroxy-3-phenylpropionic acid (5.0 g, 30.1 mmol) and p-toluenesulfonic acid hydrate (1 g) in methanol (125 mL) was refluxed with removal of water using 3A molecular sieves for 17 h. The solution was concentrated and dissolved in ether. The ether solution was washed with saturated sodium bicarbonate, brine and concentrated to provide the title compound as a white solid (5.32 g, 98%): NMR (CDC13); δ 7.36–7.20 (m, 5H), 4.47 (ddd, J=5, 6, 7 Hz, 1H), 3.78 (s, 3H), 3.14 (dd, J=5, 14 Hz, 1H), 2.97 (dd, J=7, 14 Hz), 2.69 (d, J=6Hz, 1H).

EXAMPLE 8

(R)-2-[4-(2,3-Dimethyl-1-oxa-9-thia-cyclopenta[b]fluoren-4-yl)-2,6-diiodo-phenoxy]-propionic acid Diethylazodicarboxylate (0.075 mL, 0.48 mmol) was added dropwise to a stirred, ambient temperature solution of 4-(2,3-dimethyl-1-oxa-9-thia-cyclopenta[b]fluoren-4-yl)-2, 6-diiodo-phenol (0.19 g, 0.32 mmol), methyl(-s)-(−)lactate (98%, 0.050 g, 0.48 mmol) and triphenylphosphine (0.125 g, 0.48 mmol) in benzene (1.6 mL) under a dry nitrogen atmosphere. The solution was heated in an 80° C. oil bath for 3.0 h. Upon cooling to room temperature, the reaction mixture was diluted with dichloromethane and silica gel (3 mL) was added. Solvents were removed and the silica adsorbate was flash chromatographed (eluent 9:1 petroleum ether:ethyl acetate) to provide the methyl ester as a white solid (0.113 g, 52%): Aqueous potassium hydroxide (1.0 N, 0.36 mL, 0.36 mmol) was added to a stirred solution of this methyl ester (0.110 g, 0.161 mmol) in dioxane (1.0 mL) at ambient temperature. After 32 h, the reaction mixture was quenched with 10% aqueous hydrochloride to pH 1 and further diluted with water (40 mL). Aqueous mixture was extracted with ethyl ether (50 mL). The ethyl ether extract was washed with water, dried with brine and anhydrous MgSO4, and concentrated to provide the title compound as an off-white solid (0.104 g, 96%): mp 218–219° C.: NMR (CDCl3): δ 7.97 (s, 2H), 7.85 (s, 1H), 7.81 (d, J=8, Hz, 1H), 7.34 (ddd, J=8, 7, 1 Hz, 1H), 7.12 (ddd, J=8, 7, 1 Hz, 1H), 6.87 (d, J=8 Hz, 1H), 5.46 (q, J=7 Hz, 1H, CH), 2.38 (s 3H), 1.77 (d, J=7 Hz, 3H), 1.61 (s, 3H); MS (+FAB): [M+], 667.8, [M+H]+, 668.9; Anal. Calc. for C25H18I2O4S: C, 44.93, H, 2.72, N, 0.00. Found: C, 44.77, H, 2.63, N, 0.20.

EXAMPLE 9

(R)-2-[4-(2,3-Dimethyl-1-oxa-9-thia-cyclopenta[b]fluoren-4-yl)-2,6-diiodo-phenoxy]-3-phenyl-propionic acid Prepared from 4-(2,3-dimethyl-1-oxa-9-thia-cyclopenta [b]fluoren-4-yl)-2,6-diiodo-phenol and (S)-2-hydroxy-3-phenylpropionic acid, methyl ester according to the procedure in Example 8 to provide the title compound as a white solid: mp 215–217: NMR (DMSO-d6): δ 8.17 (s, 1H), 7.94 (d, J=8 Hz, 1H), 7.85 (d, J=4 Hz, 2H), 7.39–7.30 (m, 5H), 7.22 (dd, J=7 Hz, 1H), 7.16 (dd, J=7, 1 Hz, 1H), 6.87 (d, J=8 Hz, 1H), 5.41 (s, 1H), 3.43 (dd, J=6, 1 Hz, 2H), 2.36 (s, 3H), 1.56 (s, 3H); MS (+FAB): [M+H]+, 745; Anal. Calc. for C31H22I2O4S: C, 50.02, H, 2.98, N, 0.00. Found: C, 47.59, H, 2.98, N, 0.13.

What is claimed is:
1. A compound of formula I having the structure

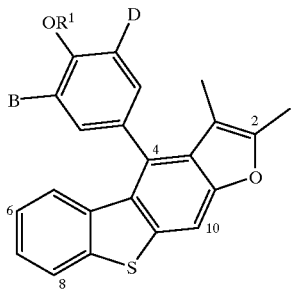

(I)

wherein
B and D are each, independently, hydrogen, halogen, —CN, alkyl of 1–6 carbon atoms, aryl, or aralkyl of 6–12 carbon atoms;
$R^1$ is —CH($R^2$)W, or 5-thiazolidine-2,4-dione;
—CH($R^2$)W represents a moiety wherein either:
1) $R^2$ is selected from —CH$_2$(1H-imidazol-4-yl), —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl) and W is selected from —CO$_2$R$^3$, —CONH$_2$, —CONHOH, —CN, CONH(CH$_2$)$_2$CN, 5-tetrazole, or —PO$_3$(R$^3$)$_2$; or
2) $R^2$ is hydrogen, alkyl of 1–6 carbon atoms, aralkyl of 6–12 carbon atoms, or aryl and W is 5-tetrazole;
$R^3$ is hydrogen, alkyl of 1–6 carbon atoms, or aryl;
or a pharmaceutically acceptable salt thereof.
2. The compound according to claim 1, wherein B and D are halogen.
3. The compound according to claim 2, wherein $R^1$ —CH($R^2$)W.
4. A method of treating metabolic disorders mediated by insulin resistance or hyperglycemia in a mammal in need thereof which comprises administering to said mammal, a compound of formula I having the structure

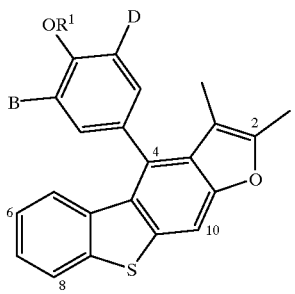

(I)

wherein
B and D are each, independently, hydrogen, halogen, —CN, alkyl of 1–6 carbon atoms, aryl, or aralkyl of 6–12 carbon atoms;
$R^1$ is —CH($R^2$)W, or 5-thiazolidine-2,4-dione;
—CH($R^2$)W represents a moiety wherein either:
1) $R^2$ is selected from —CH$_2$(1H-imidazol-4-yl), —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl) and W is selected from —CO$_2$R$^3$, —CONH$_2$, —CONHOH, —CN, CONH(CH$_2$)$_2$CN, 5-tetrazole, or —PO$_3$(R$^3$)$_2$; or 2) $R^2$ is hydrogen, alkyl of 1–6 carbon atoms, aralkyl of 6–12 carbon atoms, or aryl and W is 5-tetrazole;
$R^3$ is hydrogen, alkyl of 1–6 carbon atoms, or aryl;
or a pharmaceutically acceptable salt thereof.
5. A method of treating or inhibiting type II diabetes in a mammal in need thereof which comprises administering to said mammal, a compound of formula I having the structure

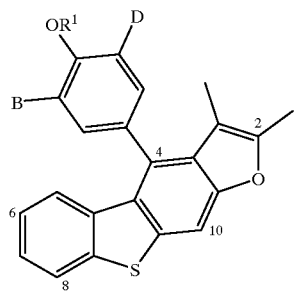

(I)

wherein
B and D are each, independently, hydrogen, halogen, —CN, alkyl of 1–6 carbon atoms, aryl, or aralkyl of 6–12 carbon atoms;
$R^1$ is —CH($R^2$)W, or 5-thiazolidine-2,4-dione;
—CH($R^2$)W represents a moiety wherein either:
1) $R^2$ is selected from —CH$_2$(1H-imidazol-4-yl), —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl) and W is selected from —CO$_2$R$^3$, —CONH$_2$, —CONHOH, —CN, CONH(CH$_2$)$_2$CN, 5-tetrazole, or —PO$_3$(R$^3$)$_2$; or
2) $R^2$ is hydrogen, alkyl of 1–6 carbon atoms, aralkyl of 6–12 carbon atoms, or aryl and W is 5-tetrazole;
$R^3$ is hydrogen, alkyl of 1–6 carbon atoms, or aryl;
or a pharmaceutically acceptable salt thereof.
6. A method of modulating glucose levels in a mammal in need thereof which comprises administering to said mammal, a compound of formula I having the structure

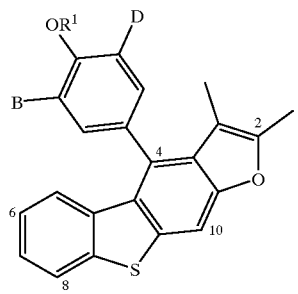

(I)

wherein
B and D are each, independently, hydrogen, halogen, —CN, alkyl of 1–6 carbon atoms, aryl, or aralkyl of 6–12 carbon atoms;
$R^1$ is —CH($R^2$)W, or 5-thiazolidine-2,4-dione;
—CH($R^2$)W represents a moiety wherein either:
1) $R^2$ is selected from —CH$_2$(1H-imidazol-4-yl), —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl) and W is selected from —CO$_2$R$^3$, —CONH$_2$, —CONHOH, —CN, CONH(CH$_2$)$_2$CN, 5-tetrazole, or —PO$_3$(R$^3$)$_2$; or 2) $R^2$ is hydrogen, alkyl of 1–6 carbon atoms, aralkyl of 6–12 carbon atoms, or aryl and W is 5-tetrazole;

$R^3$ is hydrogen, alkyl of 1–6 carbon atoms, or aryl;

or a pharmaceutically acceptable salt thereof.

7. A pharmaceutical composition which comprises a compound of formula I having the structure

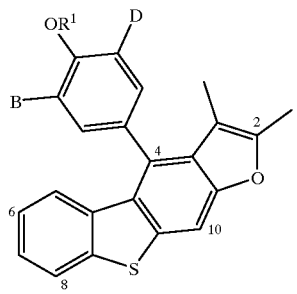

(I)

wherein

B and D are each, independently, hydrogen, halogen, —CN, alkyl of 1–6 carbon atoms, aryl, or aralkyl of 6–12 carbon atoms;

$R^1$ is —CH($R^2$)W, or 5-thiazolidine-2,4-dione;

—CH($R^2$)W represents a moiety wherein either:

1) $R^2$ is selected from —CH$_2$(1H-imidazol-4-yl), —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl) and W is selected from —CO$_2$R$^3$, —CONH$_2$, —CONHOH, —CN, CONH(CH$_2$)$_2$CN, 5-tetrazole, or —PO$_3$(R$^3$)$_2$; or 2) $R^2$ is hydrogen, alkyl of 1–6 carbon atoms, aralkyl of 6–12 carbon atoms, or aryl and W is 5-tetrazole;

$R^3$ is hydrogen, alkyl of 1–6 carbon atoms, or aryl;

or a pharmaceutically acceptable salt thereof.

* * * * *